United States Patent
Szarvas et al.

(10) Patent No.: US 8,507,419 B2
(45) Date of Patent: Aug. 13, 2013

(54) SALTS OF THIOPHOSPHORIC ACIDS AND USE THEREOF IN LUBRICANTS

(75) Inventors: Laszlo Szarvas, Ludwigshafen (DE); Dirk Gerhard, Mannheim (DE); Matthias Volkholz, Erkelenz (DE); Corvin Volkholz, Erkelenz (DE)

(73) Assignees: BASF SE, Ludwigshafen (DE); ILCO Chemikalien GmbH, Erkelenz (DE)

( * ) Notice: Subject to any disclaimer, the term of this patent is extended or adjusted under 35 U.S.C. 154(b) by 143 days.

(21) Appl. No.: 13/041,802

(22) Filed: Mar. 7, 2011

(65) Prior Publication Data

US 2011/0218130 A1 Sep. 8, 2011

Related U.S. Application Data

(60) Provisional application No. 61/311,412, filed on Mar. 8, 2010.

(51) Int. Cl.
*C10M 133/46* (2006.01)
*C10M 115/10* (2006.01)

(52) U.S. Cl.
USPC ........... 508/286; 508/243; 508/348; 508/355; 508/428

(58) Field of Classification Search
USPC .................. 508/243, 286, 348, 355, 420, 428
See application file for complete search history.

(56) References Cited

U.S. PATENT DOCUMENTS

| 4,108,858 A | * | 8/1978 | Malec | 546/347 |
| 2010/0227785 A1 | * | 9/2010 | Habeeb et al. | 508/370 |

FOREIGN PATENT DOCUMENTS

| DE | 2 131 926 | 1/1972 |
| DE | 2 221 646 | 11/1972 |
| WO | WO 2005/021484 A2 | 3/2005 |
| WO | WO 2005/113702 A1 | 12/2005 |
| WO | WO 2008/043837 A1 | 4/2008 |

* cited by examiner

*Primary Examiner* — Taiwo Oladapo
(74) *Attorney, Agent, or Firm* — Oblon, Spivak, McClelland, Maier & Neustadt, L.L.P.

(57) ABSTRACT

Salts of the anion of di-, tri- or tetrathiophosphoric acid of the formula I

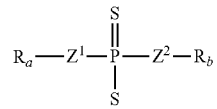

in which $Z^1$ and $Z^2$ are each independently an oxygen or sulfur atom, and $R_a$ and $R_b$ are each independently an organic group having 1 to 20 carbon atoms,
and a cation which comprises a heterocyclic ring system having one to three nitrogen atoms.

20 Claims, No Drawings

SALTS OF THIOPHOSPHORIC ACIDS AND USE THEREOF IN LUBRICANTS

The invention relates to salts of the anion of di-, tri- or tetrathiophosphoric acid of the formula I

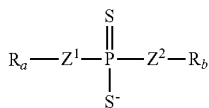

in which $Z^1$ and $Z^2$ are each independently an oxygen or sulfur atom, and $R_a$ and $R_b$ are each independently an organic group having 1 to 20 carbon atoms,
and a cation which comprises a heterocyclic ring system having one to three nitrogen atoms, and to the use of these salts in lubricants.

During the use of lubricants or hydraulic fluids, there is damage to the apparatus parts over the course of time. The damage is attributable especially to corrosion and abrasion on metal parts or wear of the metal parts.

The addition of suitable additives to lubricants, especially lubricant oils, or hydraulic fluids is intended to counteract such damage over a maximum period.

The use of metal salts of dithiophosphoric acid, especially zinc dithiophosphates, is known as such an additive. However, a disadvantage is that metal salts, especially metal oxides such as zinc oxide, form as residues during the use of such metal salts, for example in internal combustion engines. Such metal oxides form deposits on apparatus parts or pollute the environment in the form of fine dust.

Additives which burn very substantially without residue, which is also referred to as ashlessness, are therefore desired.

Salts of dithiophosphoric acid with organic cations are known from DE-A 2131926 and DE-A 2221646. Replacement of the metal salts by such organic cations is intended to achieve ashlessness.

DE-A 2131926 describes salts of a phosphonium cation and a thiophosphoric acid derivative as additives to hydraulic fluid. The salts described prevent damage to metal parts of the hydraulic system. Such damage is attributed to a wear effect of the hydraulic fluid.

DE-A 2221646 discloses lubricant oils which comprise amine salts of a thiophosphoric acid. The amine salts reduce the abrasion on plant parts. The amine cation is a quaternary ammonium cation.

For use in lubricant oils, there is a constant search for improved additives which even better meet very substantially all above demands.

It was therefore an object of the present invention to find additives, for example to lubricants or hydraulic fluids, which are easy to prepare or to obtain, have good compatibility with different lubricant oils and can therefore be used in a wide variety of different lubricants or hydraulic fluids, have very good action and significantly reduce corrosion and abrasion on metal parts, and do not form any residues, i.e. are ashless.

Accordingly, the salts of the formula I and the use thereof in lubricant oils have been found.

The inventive salts are salts of the anion of di-, tri- or tetrathiophosphoric acid of the formula I

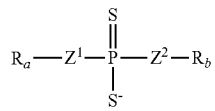

in which $Z^1$ and $Z^2$ are each independently an oxygen or sulfur atom, and $R_a$ and $R_b$ are each independently an organic group having 1 to 20 carbon atoms,
and a cation which comprises a heterocyclic ring system having one to three nitrogen atoms.

The Anion

Preferably, both $Z^1$ and $Z^2$ in formula I are an oxygen atom. The anion is therefore preferably that of a dithiophosphoric acid.

$R_a$ and $R_b$ in formula I are preferably each an organic group having 1 to 16 carbon atoms, more preferably 6 to 16 carbon atoms, where the organic group may also comprise heteroatoms, e.g. oxygen or nitrogen, preferably in the form of a hydroxyl group, ether group, or primary, secondary or tertiary amino group.

More particularly, $R_a$ and $R_b$ in formula I are each an organic group which consists exclusively of carbon and hydrogen and does not comprise any other heteroatoms, i.e. are each a hydrocarbon group. This may be an aliphatic or aromatic hydrocarbon group, but may also be a hydrocarbon group which consists both of aliphatic and of aromatic groups.

$R_a$ and $R_b$ are more preferably each independently a C1 to C20 alkyl group, especially a C1 to C16, even more preferably a C6 to C16 alkyl group and, in a particular embodiment, a C8 to C12 alkyl group.

The parent dithiophosphoric acid of the anion is obtainable in a known manner by reacting phosphorus sulfides such as $P_4S_{10}$ or $P_2S_5$ with the corresponding alcohols of the $R_a$ and $R_b$ radicals. In this reaction, it is possible to use a single alcohol or else, of course, a mixture of alcohols. In the case of use of a single alcohol, $R_a$ and $R_b$ are identical. In contrast, in the case of use of an alcohol mixture, depending on the compositions of the alcohol mixture, mixtures of compounds with a corresponding random distribution of identical and different $R_a$ and $R_b$ radicals are obtained.

Irrespective of whether $R_a$ and $R_b$ in the anion of the formula I, as a result of the preparation of the dithiophosphoric acid, are identical or different, the sum of the carbon atoms in the $R_a$ and $R_b$ radicals in a preferred embodiment is 12 to 40, more preferably 14 to 30 and most preferably 16 to 24.

More particularly, $R_a$ and $R_b$ are identical by virtue of the use of a single alcohol in the preparation of the dithiophosphoric acid.

Particularly suitable anions of the formula I include anions in which at least one of the $R_a$ and $R_b$ radicals is a 2-ethylhexyl group or a 2-propylheptyl group; very particularly suitable are the anions, in which both $R_a$ and $R_b$ radicals are a 2-ethylhexyl group or both $R_a$ and $R_b$ radicals are a 2-propylheptyl group (see formulas in the examples)

The Cation

Preference is given to a cation which comprises a heterocyclic ring system having one, two or three nitrogen atoms as part of the ring system.

Useful cations of this kind include monocyclic, bicyclic, aromatic or nonaromatic ring systems. Examples include bicyclic systems, as described in WO 2008/043837. The bicyclic systems of WO 2008/043837 are diazabicyclo derivatives, preferably composed of a 7-membered ring and a 6-membered ring, which comprise an amidinium group; a particular example is the 1,8-diazabicyclo[5.4.0]undec-7-enium cation.

Very particular preference is given to a cation with a five- or six-membered heterocyclic ring system with one, two or three nitrogen atoms as part of the ring system.

Useful organic cations of this kind include, for example pyridinium cations, pyridazinium cations, pyrimidinium cations, pyrazinium cations, imidazolium cations, pyrazolium cations, pyrazolinium cations, imidazolinium cations, thiazolium cations, triazolium cations, pyrrolidinium cations and imidazolidinium cations. These cations are detailed, for example in WO 2005/113702. If necessary for a positive charge on the nitrogen atom or in the aromatic ring system, the nitrogen atoms each bear a hydrogen atom or an organic group having generally not more than 20 carbon atoms, preferably an optionally substituted saturated or unsaturated hydrocarbon group, especially a C1 to C16 alkyl group or alkenyl group, especially a C1 to C10, and more preferably a C1 to C4 alkyl group, as substituents; the above hydrocarbon groups or alkyl groups or alkenyl groups may be substituted by functional groups, for example a hydroxyl group.

The carbon atoms of the ring system may also be substituted by organic groups having generally not more than 20 carbon atoms, preferably a hydrocarbon group, especially a C1 to C16 alkyl group or alkenyl group, especially a C1 to C10 and more preferably a C1 to C4 alkyl group; the above hydrocarbon groups or alkyl groups or alkenyl groups may in turn be substituted by functional groups, for example a hydroxyl group.

The cation is more preferably an imidazolium cation of the formula II

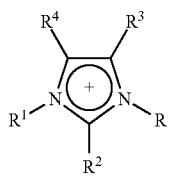

a pyridinium cation of the formula III

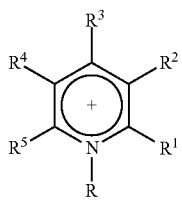

a pyrazolium cation of the formula IV

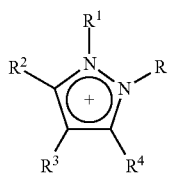

an imidazolinium cation of the formula V

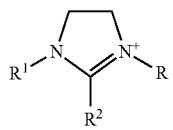

or a triazolium cation of the formula VI

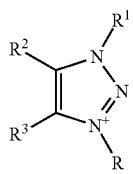

where R and R1 to R5 are each independently a hydrogen atom or an organic group having 1 to 20 carbon atoms.

In the imidazolium cations of the formula II, R and R1 are preferably each independently an organic group having 1 to 20 carbon atoms, especially having 1 to 12 carbon atoms. The organic group is preferably a hydrocarbon group with no further heteroatoms; R and R1 are especially each independently a C1 to C20 alkyl group, more preferably a C1 to C12 alkyl group, most preferably a C1 to C4 alkyl group.

The R2 to R4 radicals in formula II are each independently a hydrogen atom or an organic group having 1 to 20 carbon atoms, especially 1 to 12 carbon atoms; in the case of an organic group as a radical, preference is given in turn to a hydrocarbon group with no further heteroatoms, especially a C1 to C20 alkyl group, more preferably a C1 to C12 alkyl group, most preferably a C1 to C4 alkyl group. The R2 to R4 radicals in formula II are more preferably a hydrogen atom or a C1 to C4 alkyl group. The R2 to R4 radicals in formula II are most preferably a hydrogen atom.

In the pyridinium cations of the formula III, R is preferably an organic group having 1 to 20 carbon atoms, especially having 1 to 12 carbon atoms. The organic group is preferably a hydrocarbon group with no further heteroatoms; R is preferably a C1 to C20 alkyl group, more preferably a C1 to C12 alkyl group, most preferably a C1 to C4 alkyl group.

The R1 to R5 radicals in formula III are each independently a hydrogen atom or an organic group having 1 to 20 carbon atoms, especially 1 to 12 carbon atoms; in the case of an organic group as a radical, preference is given in turn to a hydrocarbon group with no further heteroatoms, especially a C1 to C20 alkyl group, more preferably a C1 to C12 alkyl group, most preferably a C1 to C4 alkyl group. The R1 to R5 radicals in formula III are more preferably a hydrogen atom or a C1 to C4 alkyl group. The R1 to R5 radicals in formula III are most preferably a hydrogen atom.

In the pyrazolium cations of the formula IV, R and R1 are preferably each an organic group having 1 to 20 carbon atoms, especially having 1 to 12 carbon atoms. The organic group is preferably a hydrocarbon group with no further heteroatoms; R and R1 are especially each independently a C1 to C20 alkyl group, more preferably a C1 to C12 alkyl group, most preferably a C1 to C4 alkyl group.

The R2 to R4 radicals in formula IV are each independently a hydrogen atom or an organic group having 1 to 20 carbon atoms, especially 1 to 12 carbon atoms; in the case of an organic group as a radical, preference is given in turn to a hydrocarbon group with no further heteroatoms, especially a C1 to C20 alkyl group, more preferably a C1 to C12 alkyl group, most preferably a C1 to C4 alkyl group. The R2 to R4 radicals in formula IV are more preferably a hydrogen atom or a C1 to C4 alkyl group. The R2 to R4 radicals in formula IV are most preferably a hydrogen atom.

In the imidazolinium cations of the formula V, R, R1 and R2 are preferably each a hydrogen atom or an organic group having 1 to 20 carbon atoms, especially having 1 to 18 carbon atoms; in the case of an organic group as a radical, the group is preferably a saturated or unsaturated hydrocarbon group which may optionally be substituted by one or more functional groups, for example a hydroxyl group.

Particularly preferred imidazolinium cations of the formula V are those in which one of the R or R1 radicals is a hydrogen atom and the other R or R1 radical is a C1 to C8 alkyl group or a C1 to C8 hydroxyalkyl group. R2 may especially be a saturated or unsaturated hydrocarbon radical, e.g. a C1 to C20 alkyl group or a C2 to C20 alkylene group.

One example of such an imidazolinium cation is the cation of

Amine-O (BASF trade name) of the formula

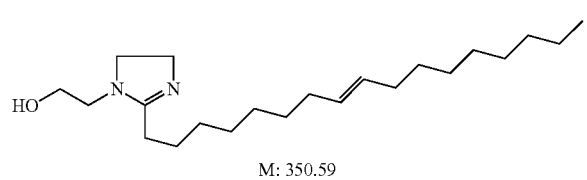 [SMILES: CCCCCCCC/C=C/CCCCCCCC1=NCCN1CCO]

M: 350.59

The cation or salt is obtainable therefrom by addition of the corresponding acid and associated addition of a hydrogen atom as the R radical onto the unsubstituted nitrogen atom.

In the triazolium cations of the formula VI, R and R1 are preferably each a hydrogen atom or an organic group having 1 to 20 carbon atoms, especially having 1 to 18 carbon atoms; in the case of an organic group as a radical, preference is given in turn to a hydrocarbon group with no further heteroatoms, especially a C1 to C20 alkyl group, more preferably a C1 to C12 alkyl group, most preferably a C1 to C4 alkyl group. The R and R1 radicals in formula VI are more preferably each a hydrogen atom or a C1 to C4 alkyl group.

The R2 and R3 radicals in formula VI are preferably each independently a hydrogen atom or an organic group having 1 to 20 carbon atoms, where the R2 and R3 radicals may also be joined to one another to form a ring system. R2 and R3 may, for example, each independently be a hydrogen atom or an organic group having 1 to 12 carbon atoms, in the case of an organic group as a radical, the group is preferably a hydrocarbon group with no further heteroatoms, especially a C1 to C20 alkyl group, more preferably a C1 to C12 alkyl group, most preferably a C1 to C4 alkyl group. The R2 and R3 radicals together may more preferably form a benzene ring, where the carbon atoms of the benzene ring may in turn optionally be substituted by organic groups, for example organic groups having 1 to 10 carbon atoms, especially C1 to C10 alkyl groups, more preferably C1 to C4 alkyl groups.

A preferred triazolium cation is, for example the cation of benzotriazole, which in turn by reaction with the desired acid and addition of a hydrogen atom as the R radical onto the corresponding nitrogen atom, as shown in formula VI.

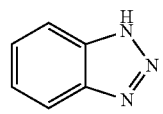

The cation is most preferably an imidazolium cation of the above formula II, where R and R1 are each independently an organic group having 1 to 20 carbon atoms, and R2, R3 and R4 are each independently a hydrogen atom or an organic group having 1 to 20 carbon atoms. With regard to the preferred organic groups, the above statements apply; more particularly, the organic groups are C1 to C12, especially C1 to C4, alkyl groups.

Examples of particularly preferred imidazolium cations include:
1-methyl-3-methylimidazolium (R and R1=methyl, R2, R3, R4=H), MMIM for short
1-ethyl-3-methylimidazolium (R=ethyl and R1=methyl, R2, R3, R4=H), EMIM for short
1-ethyl-3-ethylimidazolium (R and R1=ethyl, R2, R3, R4=H), EEIM for short
1-butyl-3-methylimidazolium (R=butyl and R1=methyl, R2, R3, R4=H), BMIM for short
1-butyl-3-ethylimidazolium (R=butyl and R1=ethyl, R2, R3, R4=H), BEIM for short
1-butyl-3-butylimidazolium (R and R1=butyl, R2, R3, R4=H), BBIM for short
1-octyl-3-methylimidazolium (R=octyl and R1=methyl, R2, R3, R4=H), OMIM for short Preparation of the Salts The inventive salts can be prepared by various known methods.

More particularly, the inventive salts can be prepared from other salts of the cation, for example from the alkylcarbonate salts or hydroxide salts.

Salts of the abovementioned cations and an alkylcarbonate as the anion, and the preparation of such salts, are known, for example from WO 2005/021484. This WO also describes the conversion of the alkylcarbonate salts to salts of other anions by addition of an acid.

According to the teaching of WO, imidazolium alkylcarbonates or the alkylcarbonates of other cations (also referred to hereinafter collectively as alkylcarbonate for short) can be converted to salts of the formula I by addition of the di-, tri- or tetrathiophosphoric acid. The reaction forms carbon dioxide.

The preferred starting compound is the imidazolium methylcarbonate as the starting material.

The di-, tri- or tetrathiophosphoric acid selected is the corresponding acid with the desired $R_a$ and $R_b$ radicals. Di-, tri- or tetrathiophosphoric acids of the formula VII

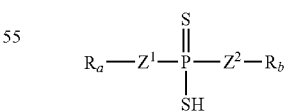

in which $Z^1$ and $Z^2$ are each independently an oxygen or sulfur atom, the $R_a$ radical is a 2-propylheptyl group and $R_b$ radical is an organic group having 1 to 20 carbon atoms, have not been described to date and, in the context of this invention, are some of the preferred phosphoric acids, especially in the form of dithiophosphoric acid ($Z^1$ and $Z^2$ are each oxygen) for preparation of the above salts. More preferably, both $R_a$ and $R_b$ radicals in formula VII are a 2-propylheptyl group. Preferred salts are salts with cations of formulas II to VI, in particular with an imidazolium cation of formula II, and the anion of formula VII.

The alkylcarbonate can be reacted with the di-, tri- or tetrathiophosphoric acid, for example, at 0 to 100° C., especially 10 to 80° C. and standard pressure, optionally in the presence of a solvent.

Suitable solvents are especially alcohols such as methanol, ethanol, isopropanol. Particular preference is given to methanol as solvent.

The alkylcarbonate and the di-, tri- or tetrathiophosphoric acid can each be used in excess. Preference is given to a molar ratio of 1:0.8 to 0.8:1.

Very particular preference is given to using the alkylcarbonate and the di-, tri- or tetrathiophosphoric acid in an approximately stoichiometric ratio.

Alternatively, the compounds of the formula I can also be prepared the to the hydroxide salt of the abovementioned cations. Here, the reaction with the di-, tri- or tetrathiophosphoric acid is effected with elimination of water.

In addition, to prepare the inventive salts, any desired metathesis reactions, i.e. anion exchange reactions, are possible, proceeding from any desired salt of an abovementioned cation and exchange of the anion for the corresponding anion of the di-, tri- or tetrathiophosphoric acid. Generally, undesired starting salts for the anion exchange are halides and especially chlorides, in view of the later use and of a possible residual content of chloride.

The inventive salts comprise preferably less than 100 pm, especially less than 20 ppm, of halides. They are more preferably free of halides.

Preferred salts are for example,

MMIM bis-2-ethylhexyldithiophosphate=MMIM [(2EH)$_2$ DTP]
MMIM bis-2-propylheptyldithiophosphate=MMIM [(2PH)$_2$ DTP]
EMIM bis-2-ethylhexyldithiophosphate=EMIM [(2EH)$_2$ DTP]
EMIM bis-2-propylheptyldithiophosphate=EMIM [(2PH)$_2$ DTP]
EEIM bis-2-ethylhexyldithiophosphate=EEIM [(2EH)$_2$ DTP]
EEIM bis-2-propylheptyldithiophosphate=EEIM [(2PH)$_2$ DTP]
BMIM bis-2-ethylhexyldithiophosphate=BMIM [(2EH)$_2$ DTP]
BMIM bis-2-propylheptyldithiophosphate=BMIM [(2PH)$_2$ DTP]
BEIM bis-2-ethylhexyldithiophosphate=BEIM [(2EH)$_2$ DTP]
BEIM bis-2-propylheptyldithiophosphate=BEIM [(2PH)$_2$ DTP]
BBIM bis-2-ethylhexyldithiophosphate=BBIM [(2EH)$_2$ DTP]
BBIM bis-2-propylheptyldithiophosphate=BBIM [(2PH)$_2$ DTP]
OMIM bis-2-ethylhexyldithiophosphate=OMIM [(2EH)$_2$ DTP]
OMIM bis-2-propylheptyldithiophosphate=OMIM [(2PH)$_2$ DTP]
and mixtures of the formula [cation] [(2EH)$_x$(2PH)$_y$DTP] where x+y=2.

In addition, it is also possible to use other mixtures.

The salt of the formula I is preferably an ionic liquid, i.e. the salt has a melting point of less than 100° C., often even less than 20° C. After removal of the solvent, the salts can therefore be transported, stored and used in a simple manner, in the form of liquids.

Use

The inventive salts or compositions which comprise an inventive salt are suitable as lubricants. In this context, a lubricant is understood to mean any substance which is used to prevent or to reduce frictional influences between surfaces moving relative to one another.

More particularly, the inventive salts are suitable as additives to customary lubricants, whether they be liquid lubricants (lubricant oils), solid lubricants, pastes or greases under standard conditions (20° C., 1 bar).

Solid lubricants are, for example, low-friction coatings, graphite, metal sulfides such as molybdenum sulfide or metal oxides ($TiO_2$, ZnO, inter alia).

Typical lubricant oils are compositions which comprise, as a main constituent, an oil or mixture of oils and optionally also further additives, or consist exclusively of an oil or mixture of oils.

In a particular embodiment, the lubricants are lubricant oils which consist to an extent of more than 50% by weight of at least one animal oil, vegetable oils, mineral oils or synthetic oil, or mixtures thereof.

Suitable oils are animal or vegetable oils or mineral oils; they may also be synthetic oils which can be prepared from a wide variety of different starting compounds, especially also from the above animal, vegetable oils or mineral oils.

The oils, for example mineral oils, may be acyclic and/or cyclic, saturated and/or unsaturated hydrocarbons which may optionally comprise one or more heteroatoms, for example O, F, P, N, S.

Examples of oils without heteroatoms include alkylbenzenes, cycloalkanes, polyalphaolefins and copolymers of unsaturated hydrocarbons; oils which comprise oxygen as a heteroatom include alcohols, esters, ketones, furans, polyethers and copolymers of olefins and, for example, acrylates, maleates or fumarates; oils which comprise fluorine and oxygen as heteroatoms include perfluoro ethers or esters; oils which comprise phosphorus and oxygen as heteroatoms include phosphoric esters; oils, which comprise phosphorus and nitrogen as heteroatoms include phosphazenes; oils which comprise sulfur or nitrogen as heteroatoms, include thiophenes.

The compounds mentioned are preferably liquid within the temperature range of application, which may be in the range from −80° C. to +450° C. (1013 mbar), but need not necessarily be a liquid in the case of particular requirements (e.g. low-friction coatings). The lubricant oils comprise the oils, for example, in an amount of 1 to 99.9% by weight. The compositions or lubricant oils may comprise additives if required, which fulfill, for example, the following tasks: aging protection, wear protection, extreme pressure additives, corrosion protection, detergents, dispersants, demulsification, emulsification, antifoams, and further tasks described in the literature (see also in "Lubricant additives: chemistry and applications/editor Leslie R. Rudnick, —2nd edition, 2009, CRC Press").

Animal or vegetable oils are, for example, rapeseed oil, castor oil or fish oil.

Useful mineral oils include, for example, mineral oil fractions from spindle oils up to SAE 30, 40 or 50 lubricant oils.

Synthetic oils are especially oils which are obtainable by esterifying or etherifying suitable starting materials, for example including the aforementioned animal or vegetable oils or mineral oils. Examples include diesters, as obtainable by esterification of dicarboxylic acids such as adipic acid or sebacic acid with monohydric alcohols, or oligoesters, which are obtainable by esterification of mixtures of di- or oligocarboxylic acids, di- or oligoalcohols and monoalcohols, for example oligoesters of sebacic acid or adipic acid, a polyglycol and a monohydric alcohol such as 2-ethylhexanol.

Synthetic oils are, for example, oligomers which are liquid even under standard conditions, (20° C., 1 bar) and are obtainable by polymerization, whether by free-radical polymerization, polycondensation or other polyadduct formation, of monomers. Useful examples are oligomers based on ethylene oxide, propylene oxide, alkenes or isoalkenes, such as polyethylene glycols, polypropylene glycols, polyisobutylenes, or polymers and copolymers obtainable by free-radical polymerization of ethylenically unsaturated monomers, for example based on vinyl ethers, vinyl esters, acrylic esters, meteates, fumarates, etc.

The lubricants, or lubricant oils, find use, for example, as motor oils (gasoline and diesel engines), transmission oils, chain lubricants or lubricant greases. The list is only intended to indicate customary uses of lubricants by way of example.

In addition, the inventive salts or compositions which comprise an inventive salt are suitable as or in hydraulic fluids, damping fluids or force transmission media.

The inventive salts are suitable as an additive for compositions which are used in applications in which there is, or there is a risk of, corrosion and abrasion on apparatus parts.

It is also possible to use mixtures of the inventive salts as additives.

The compositions which are used, for example, as lubricants, or lubricant oils, hydraulic fluids, damping fluids or force transmission media preferably comprise at least 0.1% by weight, more preferably at least 0.2% by weight, of the inventive salts, whether it be only one inventive salt or a mixture of two or more inventive salts. In general, a maximum content of 20% by weight, especially of 10% by weight, or especially 5% by weight or more preferably of 3% by weight is sufficient.

It should be noted that, in all above uses, aqueous systems are also useful, especially biphasic systems composed of an aqueous phase and a nonaqueous phase, in which the salt of the di-, tri- or tetrathiophosphoric acid is preferably present in the nonaqueous phase.

Lubricants may especially have a content of 0.1 to 20% by weight, more preferably of 0.2 to 10% by weight, most preferably of 0.3 to 5% by weight, of the inventive salts.

Preferred inventive salts are ionic liquids (see above); for this reason, they can also be used directly themselves as a lubricant oil, hydraulic medium, damping fluid or other force transmission media.

The inventive salts can also be mixed with other ionic liquids or dissolved therein. Other ionic liquids include salts of the above cations, for example of the pyridinium cations, pyrazolium cations or especially of the imidazolium cations of the formulae II, III and IV with any anions. Examples of such anions include chloride, bromide, hydrogensulfate, tetrachloroaluminate, thiocyanate, dicyanamide, methylsulfate, ethylsulfate, methanesulfonate, formate, acetate, dimethylphosphate, diethylphosphate, p-tolylsulfonate, tetrafluoroborate and hexafluorophosphate, methylmethylphosphonate and methylphosphonate.

The invention therefore also relates to compositions which consist of ionic liquids to an extent of at least 20% by weight, especially to an extent of at least 50% by weight and more preferably to an extent of at least 70% by weight, and comprise inventive salts, preferably in an amount of at least 0.1% by weight, especially at least 0.5% by weight, most preferably in an amount of at least 1% by weight, based on the composition.

The inventive salt may be dissolved in the ionic liquid; the preferred maximum content then corresponds to that mentioned above of 20% by weight.

More particularly, the inventive salt in these compositions is itself an ionic liquid. In this case, the content thereof in the mixture with other ionic liquids may be as high as desired and may be up to 100% by weight; such compositions may, for example, also consist of inventive salts to an extent of 0.1 to 90% by weight, especially 0.5 to 50% by weight, of 10 to 99.9% by weight, especially 50 to 99.5% by weight, of other ionic liquids, and optionally 0 to 70% by weight, especially 0 to 50% by weight, of further additives or solvents where the total content of ionic liquids in the composition is preferably at least 20% by weight, more preferably at least 50% by weight.

The above compositions which consist of ionic liquids to an extent of at least 20% by weight are also correspondingly suitable, with the same advantages already detailed above, as a lubricant oil, hydraulic fluid, damping fluid or other force transmission medium.

In summary, it can be stated that, when the inventive salts composed of the anion of the di-, tri- or tetrathiophosphoric acid are employed in the above uses, for example in lubricant oils, the following advantages arise:

better protection against wear on plant parts (antiwear performance)

a high level of protection against oxidation of the oils promotion of the action of other additives, e.g. phosphoric esters (synergistic action)

a relatively low content of sulfur and phosphorus in the formulation ashlessness, i.e. there is no emission of fine metal oxide dusts, as observed in the case of use of metal salts in internal combustion engines of all types, for example gasoline and diesel engines. This results in better environmental compatibility, and an improvement in the frictional behavior compared to conventional antiwear additives, which also leads, for example, to a longer lifetime and to saving of energy.

The above effects can be achieved even at a low content of the inventive salts in the compositions. Suitable compositions, especially those for the above uses, comprise preferably not more than 0.15 mol of phosphorus and 0.25 mol of sulfur and more preferably not more than 0.1 mol of phosphorus and 0.2 mol of sulfur per kg of composition; they preferably comprise at least 0.01 mol of phosphorus, more preferably at least 0.05 mol of phosphorus and at least 0.01 mol of sulfur and more preferably at least 0.05 mol of sulfur, where all molar amounts are based on 1 kilogram (kg) of composition, for example lubricants.

The salts of the invention can replace metal salts in particular zinc salts, for example zinc dithiophosphates, completely. Therefore, in a preferred embodiment of the invention, the compositions, lubricant, lubricant oil, hydraulic fluid, damping fluid and force transmission fluids comprise less than 0.2% by weight, more preferred less than 0.1%, and most preferred less than 0.05% by weight of zinc cations. In a very particular preferred embodiment of the invention they are free of zinc cations.

EXAMPLES

Preparation

Preparation of Inventive Imidazolium Dithiophosphates

A 1,3-dialkylimidazolium methylcarbonate dissolved in methanol was initially charged and admixed dropwise with dialkyldithiophosphoric acid in an approximately stoichiometric ratio at 50° C. while stirring. In the course of this there was significant evolution of gas. After the end of addition, the reaction mixture was stirred at 50° C. for another hour. The solvent was removed under reduced pressure and elevated temperature, and the product was obtained as a pure substance.

The 1,3 dialkylimidazolium methylcarbonates used were:
EMIM methylcarbonate
OMIM methylcarbonate The dialkyldithiophosphoric acids used were:
di-2-ethylhexyldithiophosphoric acid (Deophos®, D.O.G. Hamburg)
di-2-propylheptyldithiophosphoric acid

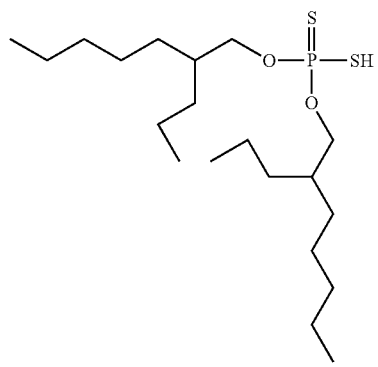 [SMILES: CCCCCC(CCC)COP(=S)(S)OCC(CCC)CCCCC]

The reaction proceeds by the following mechanism, shown using the example of di-2-ethylhexyldithiophosphoric acid and of EMIM methylcarbonate:

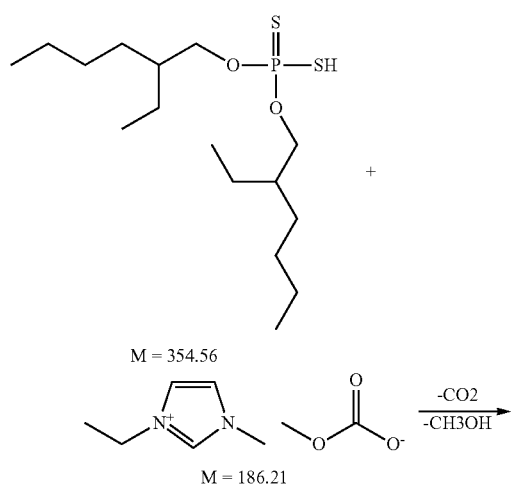

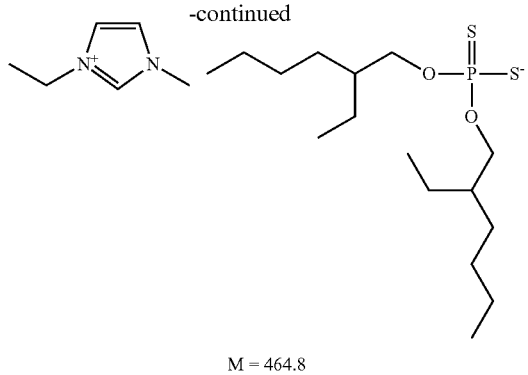

M = 464.8

Preparation Example 1

Preparation of EMIM di-2-ethylhexyldithiophosphate [EMIM] [2EHDTP]

155 g of EMIM methylcarbonate solution (46.6 g=0.25 mol of EMIM methylcarbonate in methanol) were initially charged, and 90.4 g=0.255 mol of Deophos were slowly added dropwise at 50° C. while stirring. The reaction starts up immediately, and $CO_2$ escapes.

After the end of addition, the mixture was stirred at 50° C. for about another 1 h, until no further gas evolution was visible.

The product was concentrated to dryness on a rotary evaporator.

Final weight 118.9 g

The NMR data and elemental analysis agreed with EMIM di-2-ethylhexyldithiophosphate.

Preparation Example 2

Preparation of OMIM di-2-ethylhexyldithiophosphate [OMIM] [2EHDTP]

162.4 g of OMIM methylcarbonate solution (53.6 g=0.2 mol of OMIM in methanol) were initially charged, and 70.9 g (0.2 mol) of Deophos were slowly added dropwise at 50° C. while stirring. In the course of this, $CO_2$ escapes. After the end of addition, the mixture was stirred at 50° C. for about another 1 h until no further gas evolution was visible.

The product was concentrated to dryness on a rotary evaporator.

Final weight 109.7 g of yellow, high-viscosity liquid

The NMR data and elemental analysis agreed with OMIM di-2-ethylhexyldithiophosphate.

Preparation Example 3

Preparation of di(2-propylheptyl)dithiophosphoric acid 0.2 mol of diphosphorus pentasulfide (44 g) was suspended in 300 ml of toluene and heated to 75° C. Then 0.8 mol of 2-propylheptanol (127 g) was added dropwise with evolution of gas over a period of 1 h. The reaction mixture was stirred at 75° C. for a further 2 hours. A clear solution was obtained. The conversion was >95% (determined by means of acid-base titration).

Performance Tests:
Load Carrying Capacity

The load carrying capacity was determined analogously to ASTM D 5706 (staged test).

In the vibration-friction-wear instrument, abbreviated to SRV instrument in German (Optimol Instruments, Munich) the composition to be tested is applied to a disk and a ball is pressed onto it with a defined, rising load, the composition serving as the lubricant between plate and ball. The load is increased stepwise until a coefficient of friction of 0.25 is exceeded.

Conditions: distance 1 mm, frequency 50 hertz, temperature: room temperature, ball-disk specimen geometry, test load: running-in time: 50 N-30 sec, then rising in 100 N steps until the coefficient of friction is >0.25.

The measurements are stopped automatically as soon as it is clear that the coefficient of friction begins to jump to a high value, i.e. on commencement of damage to the disk or ball owing to the lack of action of the composition as a lubricant. The load applied on stoppage (in force per unit area, N/mm²) is referred to as OK load; the higher the OK load, the better the lubricity.

Oxidation Behavior

To determine the oxidation behavior, a DSC analysis was performed under air. The composition was introduced into a glass vessel and the temperature was increased from 30° C. to 410° C., and the amount of heat released by oxidation (exothermic reaction) was determined. The higher the amount of heat, the more intensive the oxidation. The lower the measured amount of heat, the better is the oxidation behaviour.

The lubricant oils (base oils) used were products customary on the market, such as DITA, Palatinol 10P, Synative ES TMTC.

For comparison, the additive used was the zinc salt customary on the market zinc (di-2-ethylhexyldithiophosphate)₂ (=Zn [2EHDTP]2); owing to the divalency of zinc, the zinc salts comprise two dithiophosphate anions.

Load Carrying Capacity

|  | OK load N/mm² | Additive [% by wt.] | Additive |
|---|---|---|---|
| DITA (diisotridecyl adipate) | 100% | 1130 |  |
| DITA | 99.50% | 2000 | 0.50% | EMIM 2EHDTP |
| DITA | 98.26% | 2080 | 1.74% | OMIM 2EHDTP |
| DITA | 98.10% | 2320 | 1.90% | EMIM 2EHDTP |
| DITA | 98.92% | 1300 | 1.08% | Zn[(2EHDTP)]2 |
| OTHER BASE OILS | 100% | 1140 |  |
| Palatinol 10P (BASF) |  |  |  |
| Synative ES TMTC (Cognis) trimethylolpropane C8-C10 ester | 100% | 1190 |  |

Oxidation behavior (DSC)

|  |  | Evolution of heat as a result of oxidation [mJ] | Additive [% by wt.] | Additive |
|---|---|---|---|---|
| DITA | 100% | 4166 |  |  |
| DITA | 99.50% | 2531 | 0.50% | EMIM 2EHDTP |
| DITA | 98.26% | 1208 | 1.74% | OMIM 2EHDTP |
| DITA | 98.10% | 101 | 1.90% | EMIM 2EHDTP |
| DITA | 98.92% | 1870 | 1.08% | Zn [(2EHDTP)]2 |

Combined systems: synergism with aryl phosphates, tert-butylated.

|  |  | OK load [N/mm²] | Evolution of heat as a result of oxidation [mJ] |
|---|---|---|---|
| DITA | 98.03% |  |  |
| Aryl phosphate A | 1.02% | 2646 | 1204 |
| EMIM 2EHDTP | 0.95% |  |  |
| DITA | 97.98% |  |  |
| Aryl phosphate A | 1.01% | 2504 | 249 |
| OMIM 2EHDTP | 1.01% |  |  |
| IONIC LIQUIDS |  |  |  |
| EMIM 2EHDTP | 100% | 1108 |  |
| OMIM 2EHDTP | 100% | 1400 |  |

The invention claimed is:

1. A salt of an anion of di-, tri- or tetrathiophosphoric acid of formula I

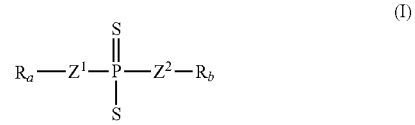

in which $Z^1$ and $Z^2$ are each independently an oxygen or sulfur atom, and $R_a$ and $R_b$ are each independently an organic group having 1 to 20 carbon atoms, and a caution, wherein the cation is an imidazolium cation of formula II

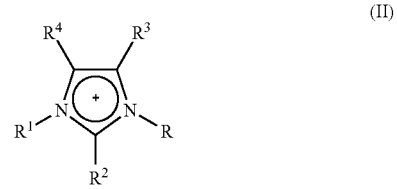

where R and R1 are each independently an organic group having 1 to 20 carbon atoms, and R2, R3 and R4 are each independently a hydrogen atom or an organic group having 1 to 20 carbon atoms.

2. A salt according to claim 1, wherein $Z^1$ and $Z^2$ in formula I are each an oxygen atom.

3. A salt according to claim 1, wherein $R_a$ and $R_b$ in formula I are each independently a C1 to C20 alkyl group.

4. A salt according to claim 1, wherein a sum of the carbon atoms in the $R_a$ and $R_b$ radicals is 12 to 40.

5. A salt of an anion of di-, tri- or tetrathiophosphoric acid of formula I

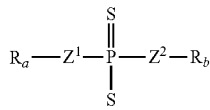

(I)

in which $Z^1$ and $Z^2$ are each independently an oxygen or sulfur atom, and $R_a$ and $R_b$ are each independently an organic group having 1 to 20 carbon atoms,
and a cation which comprises a heterocyclic ring system having one to three nitrogen atoms,
wherein one of the $R_a$ and $R_b$ radicals is, or both $R_a$ and $R_b$ radicals are, a 2-propylheptyl group.

6. A salt according to claim 5, wherein the cation is an imidazolium cation of formula II

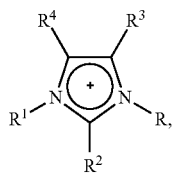

(II)

a pyridinium cation of formula III

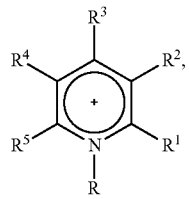

(III)

a pyrazolium cation of formula IV

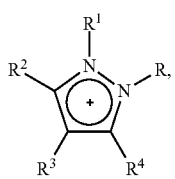

(IV)

an imidazolinium cation of formula V

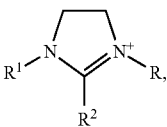

(V)

or a triazolium cation of formula VI

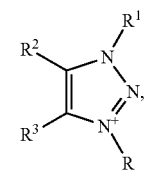

(VI)

where R and R1 to R5 are each independently a hydrogen atom or an organic group having 1 to 20 carbon atoms.

7. A process for preparing the salt according to claim 1, which comprises reacting an alkylcarbonate salt of the cation with the di-, tri- or tetrathiophosphoric acid.

8. A lubricant comprising the salt according to claim 1.

9. A lubricant comprising 0.1 to 20% by weight of the salt according to claim 1.

10. The lubricant according to claim 8, which is a room-temperature liquid lubricant which comprises more than 50% by weight of at least one selected from the group consisting of an animal oil, a vegetable oil, a mineral oil, and a synthetic oil.

11. A hydraulic fluid, damping fluid or force transmission medium comprising the salt according to claim 1.

12. A composition which comprises:
the salt according to claim 1; and
at least 20% by weight of an ionic liquid.

13. A composition which comprises:
the salt according to claim 1; and
at least 50% by weight of an ionic liquid.

14. A lubricant, hydraulic fluid, damping fluid or force transmission medium comprising the composition of claim 12.

15. A salt according to claim 1, wherein $R_a$ and $R_b$ are each independently an organic group having 6 to 16 carbon atoms.

16. A salt according to claim 1, wherein $R_a$ and $R_b$ in formula I are each independently a C1 to C16 alkyl group.

17. A salt according to claim 1, wherein $R_a$ and $R_b$ in formula I are each Independently a C6 to C16 alkyl group.

18. A salt according to claim 1, wherein $R_a$ and $R_b$ in formula I are each independently a C8 to C12 alkyl group.

19. A salt according to claim 1, wherein a sum of the carbon atoms in the $R_a$ and $R_b$ radicals is 14 to 30.

20. A salt according to claim 1, wherein a sum of carbon atoms in the $R_a$ and $R_b$ radicals is 16 to 24.

* * * * *